(12) United States Patent
Mignot et al.

(10) Patent No.: US 12,419,781 B2
(45) Date of Patent: Sep. 23, 2025

(54) METHOD AND APPARATUS FOR CONTROLLING THE INNER TEMPERATURE OF A PATIENT

(71) Applicant: Vither Hyperthermia B.V., Nijkerk (NL)

(72) Inventors: Marcel Henri Mignot, Blaricum (NL); Cornelis Watze Bottema, Phra Yuen District (TH); Robbert Renald Rudolf Nix, Zürich (CH); Ronald Albertus Arnoldus Van Doorn, Zwolle (NL)

(73) Assignee: Vither Hyperthermia B.V., Nijkerk (NL)

( * ) Notice: Subject to any disclaimer, the term of this patent is extended or adjusted under 35 U.S.C. 154(b) by 1496 days.

(21) Appl. No.: 16/750,681

(22) Filed: Jan. 23, 2020

(65) Prior Publication Data

US 2020/0155346 A1 May 21, 2020

Related U.S. Application Data

(62) Division of application No. 14/895,685, filed as application No. PCT/NL2014/050352 on Jun. 3, 2014, now Pat. No. 10,575,985.

(30) Foreign Application Priority Data

Jun. 4, 2013 (NL) ..................................... 2010911

(51) Int. Cl.
*A61F 7/12* (2006.01)
*A61B 34/10* (2016.01)
(Continued)

(52) U.S. Cl.
CPC ............... *A61F 7/12* (2013.01); *A61B 34/10* (2016.02); *A61F 7/0085* (2013.01);
(Continued)

(58) Field of Classification Search
CPC . A61B 34/10; A61B 2034/105; A61F 7/0085; A61F 2007/0054;
(Continued)

(56) References Cited

U.S. PATENT DOCUMENTS

| | | | | |
|---|---|---|---|---|
| 5,730,720 A | * | 3/1998 | Sites | G16H 20/40 604/27 |
| 6,146,411 A | * | 11/2000 | Noda | A61F 7/12 607/105 |

(Continued)

FOREIGN PATENT DOCUMENTS

| | | |
|---|---|---|
| SU | 906577 A1 * | 2/1982 |
| WO | WO9706840 A1 | 2/1997 |
| WO | WO2010111778 A1 | 10/2010 |

*Primary Examiner* — Kaitlyn E Smith
*Assistant Examiner* — Yasamin Ekrami
(74) *Attorney, Agent, or Firm* — Darya C. Cheng; Bret E. Field; Bozicevic, Field & Francis LLP

(57) ABSTRACT

The invention relates to a method and apparatus for controlling the inner temperature of a patient, comprising the steps of creating a fluid circuit that comprises a patient and a heat exchanger, the power supply thereto being controlled by a controller; subjecting at least a portion of the fluid in said circuit to the heat exchanger; directing the subjected fluid to and into the patient to control the temperature of the patient; estimating the organ temperature of the patient by a model that has been obtained on a mammal other than the patient; and controlling the power supply to the heat exchanger such that the estimated organ temperature does not exceed a threshold organ temperature, potentially taking into account estimated future organ temperatures. The invention further relates to a method and apparatus for controlling the inner temperature of a patient when subject to whole body hyperthermia, and to a method for obtaining the model.

14 Claims, 1 Drawing Sheet

(51) Int. Cl.
*A61F 7/00* (2006.01)
*A61F 7/02* (2006.01)

(52) U.S. Cl.
CPC . *A61B 2034/105* (2016.02); *A61F 2007/0054* (2013.01); *A61F 2007/0056* (2013.01); *A61F 2007/0069* (2013.01); *A61F 2007/0086* (2013.01); *A61F 2007/0093* (2013.01); *A61F 2007/0096* (2013.01); *A61F 2007/0288* (2013.01); *A61F 2007/126* (2013.01)

(58) Field of Classification Search
CPC ...... A61F 2007/0056; A61F 2007/0069; A61F 2007/0086; A61F 2007/0093; A61F 2007/0096; A61F 2007/0288; A61F 2007/126
See application file for complete search history.

(56) References Cited

U.S. PATENT DOCUMENTS

| | | | |
|---|---|---|---|
| 6,579,496 B1 | 6/2003 | Fausset et al. | |
| 7,189,253 B2* | 3/2007 | Lunderqvist | A61F 7/123 607/104 |
| 2004/0059212 A1* | 3/2004 | Abreu | A61B 5/14551 374/E13.002 |
| 2004/0267339 A1* | 12/2004 | Yon | A61F 7/12 607/113 |
| 2005/0090881 A1* | 4/2005 | Frank | A61F 7/12 607/113 |
| 2009/0105605 A1* | 4/2009 | Abreu | A61B 5/4076 600/549 |
| 2009/0156924 A1* | 6/2009 | Shariati | A61B 5/7221 600/365 |

* cited by examiner

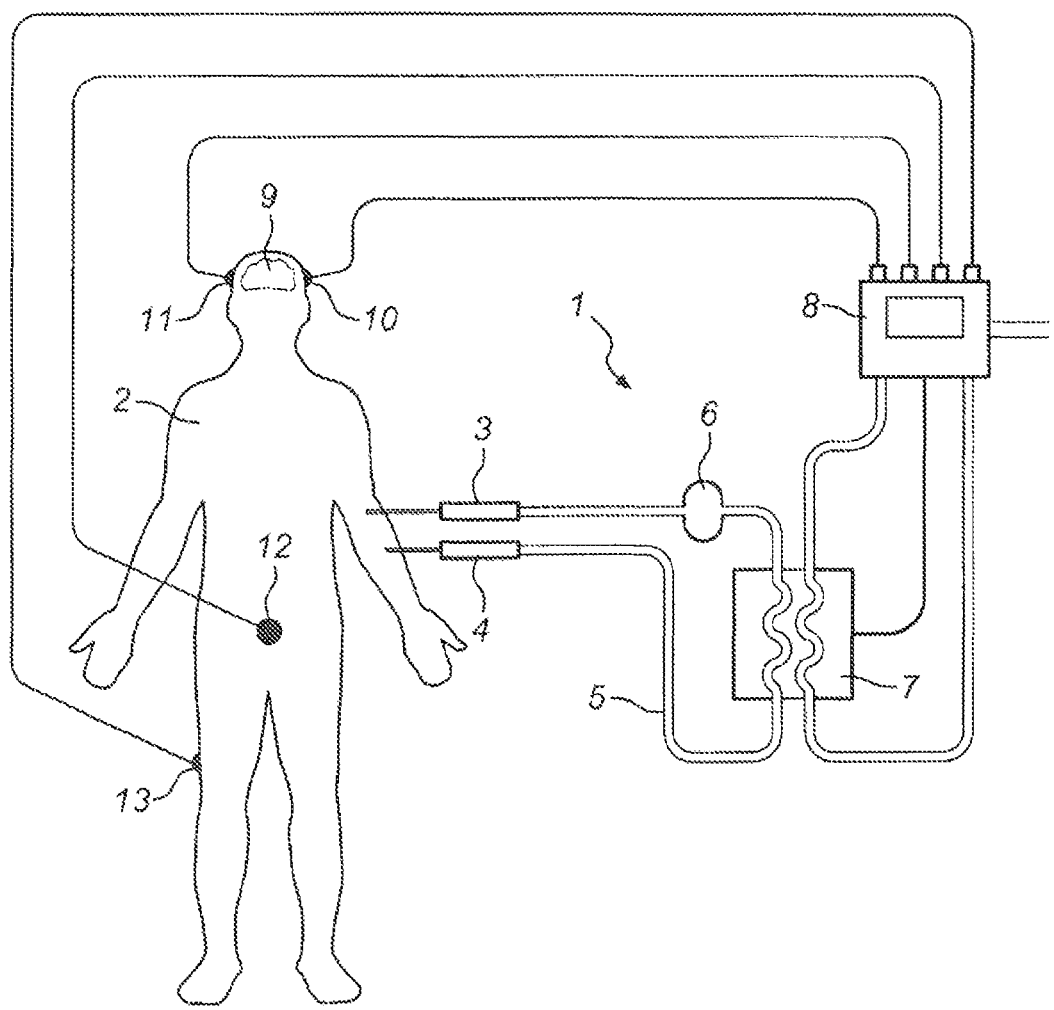

METHOD AND APPARATUS FOR CONTROLLING THE INNER TEMPERATURE OF A PATIENT

The present invention relates to a method and apparatus for controlling the inner temperature of a patient. The invention further relates to a method and apparatus for controlling the inner temperature of a patient when subject to whole body hyperthermia. The invention also relates to a method for obtaining a model for estimating the temperature of an organ of a patient.

The increase or decrease of the core temperature of a patient is a well-known treatment for several diseases, and has been applied since the 1960s. The increase of core temperature, or hyperthermia, has already been applied in several ways. U.S. Pat. No. 5,354,277 and WO 00/71072 for example both disclose a method for inducing hyperthermia in humans, wherein the core temperature of the patient is raised to 41.5°-42° C. With core temperature is meant an average core body temperature which, for humans in rest, is about 37° C. A specific single core temperature is less likely to exist, since different parts of the body may have different temperatures.

In the treatment of patients by increasing the core temperature, it is vital that the temperatures in the organs of the patient stay below a certain upper threshold value. On the other hand, temperature should be as high as possible to obtain an efficient treatment. The most important organ of which the temperature should stay below this threshold value is the brain. In Whole Body Hyperthermia for example, a patient can be exposed to a temperature of 43° C. for longer periods of time. However, when a patient is exposed to a temperature of 44° C. for more than half an hour, the patient could suffer from brain damage. In particular, it has been established that the temperature in the brain should not exceed 43° C.

WO 97/06840 A1 discloses a method and apparatus for controlling the inner temperature of a patient. The disclosed method inter alia comprises establishing a fluid circuit through a patient, the temperature of which is controlled by a heat exchanger such that the internal temperature remains below a certain threshold value. Several temperatures are measured on the body and the controller acts on a large number of measured temperature differences. The method and apparatus of WO 97/06840 A1 lacks accuracy in predicting a patient's organ temperature.

U.S. Pat. No. 6,579,496 B1 discloses an apparatus for subjecting a patient to whole body hyperthermia. The apparatus comprises a pump, a reservoir kept at a temperature of about 52° C., and a computerised control circuit comprising at least a pressure sensor, a temperature sensor and an alarm, and is adapted to reach the desired patient temperature in less than 20 minutes. U.S. Pat. No. 6,579,496 B1 does not disclose any means for estimating an organ temperature, such as the temperature of the brain.

WO 2010/111778 A1 discloses a method and apparatus for controlling brain temperature in a patient when subjected to a heated fluid circuit. As with WO 97/06840 A1, several temperatures are measured on the body. According to paragraph 223 and further, the heat supplied to the patient is controlled on the basis of the measured temperature of the blood stream entering the patient's body, the temperature of the blood stream exiting the brain, and the core temperature of the patient. The accuracy of the method and apparatus of WO 2010/111778 A1 in predicting a patient's organ temperature can be improved.

The prior art methods and devices are less apt in keeping the risk for internal organ damage sufficiently low and controllable in particular.

It is therefore a goal of the present invention to overcome the drawbacks of the prior art, or at least to offer a suitable alternative to control an organ temperature inside a patient, in particular brain temperature, in particular when subject to whole body hyperthermia.

The invention thereto proposes a method for controlling the inner temperature of a patient, e.g. to prevent damage to an organ, comprising the steps of creating a fluid circuit that comprises a patient and a heat exchanger, the power supply thereto being controlled by a controller; subjecting at least a portion of the fluid in said circuit to the heat exchanger; directing the subjected fluid to and into the patient to control the temperature of the patient; estimating the temperature of an organ of the patient; and controlling the power supply to the heat exchanger such that the estimated organ temperature remains below an upper threshold organ temperature and/or above a lower threshold organ temperature. Estimating the temperature of the organ of the patient at a time t is preferably carried out by a model that has been obtained on a mammal that differs from the patient, preferably a mammal, more preferably a pig.

Such a method wherein the estimated organ temperature is a parameter of the controlling mechanism makes it possible to ensure that the organ temperature does not exceed damaging limits. When the estimated organ temperature for instance exceeds or tends to exceed a certain threshold temperature, the power supplied to the heat exchanger can be reduced such that the fluid in the fluid circuit is no longer subjected to exchange of thermal energy with the heat exchanger. This prevents the body temperature, and therefore the organ temperature to increase further, preventing damage to the organ, as will be explained in more detail below.

Although the previous paragraphs explicitly mention keeping the brain below a certain threshold temperature, the invention is equally suited for controlling the temperature of organs other than the brain, both for hyperthermia (heating the body) as hypothermia (cooling the body and preventing temperatures from falling below a certain threshold value).

The method according to the invention is particularly suitable for controlling the temperature when patients are subjected to whole body hyperthermia, wherein the temperature of the body of a patient is increased in order to speed up treatment of certain diseases, but wherein the organ temperature, and in a preferred method the brain temperature, of the patient should not exceed damaging limits. The invention therefore also relates to a method for controlling the inner temperature of a patient when subject to whole body hyperthermia, comprising the steps of creating a fluid circuit that comprises a patient and a heat exchanger, the power supply thereto being controlled by a controller; subjecting the patient to whole body hyperthermia by subjecting at least a portion of the fluid in said circuit to the heat exchanger; and directing the subjected fluid to and into the patient to control the temperature of the patient; estimating the organ temperature of the patient; and controlling the power supply to the heat exchanger such that the estimated organ temperature remains below a threshold organ temperature.

A typical way in which the method functions is that a desired blood temperature for a body is set, the body is hooked to a whole body hyperthermia device wherein a blood vessel is bypassed by a fluid circuit which includes a heat exchanger. The heat exchanger is for instance set to heat up the blood running through, wherein a controller controls the power supplied to the heat exchanger. When the controller determines, based on the estimated organ temperature, that the organ temperature is likely to exceed a certain threshold value, the controller turns off power to the heat exchanger, in order to prevent the organ temperature from exceeding damaging limits. The desired organ temperature is the highest temperature of the blood compatible with not exceeding certain threshold values. The threshold values are determined by the maximum allowable temperature of the blood itself and those of selected organs.

A heat exchanger is preferably used since it enables the use of separate conduits. Therefore, the method can also be used to cool down the patient, in which the heat exchanger could be set to remove heat from the blood of the patient in order to, for instance, slow down cellular processes in the patient. In that case the organ temperature is to remain above a minimum threshold value, instead of remaining below a maximum threshold value.

In an embodiment of the invention, the model comprises a parametric correlation function of the temperature of the organ for which the temperature is to be controlled, and a number of input parameters. In an aspect of the invention, the parametric correlation function is obtained on a mammal other than the patient, more preferably an animal, as will be elucidated further below. The correlation function is established for a mammal organ corresponding to the organ of a patient for which the temperature is to be estimated. The input parameters should further substantially be the same.

In an embodiment of the present invention the current organ temperature of the patient at a time t is estimated by measuring input parameters comprising the temperature of at least one body part of the patient other than the organ, and the power supplied to the heat exchanger prior to time t. Taking into account the power supplied to the heat exchanger before time t improves the organ temperature estimate since it gives due account to the time lag that exists between the actual heating (or cooling) of the fluid in the fluid circuit, and the subsequent increase (or decrease) in organ temperature. The power supplied to the heat exchanger corresponds to the thermal energy exchanged with the fluid in the fluid circuit before time t. This amount of heat can for instance be calculated by dividing a relevant time period before time t in a number of periods, say 10 periods of time, an assign a different (constant) heat output to each period. The amount of time periods depend on the contribution each period makes to the organ temperature estimate. The use of a parametric correlation function also allows taking into account estimated future organ temperatures in controlling the heat exchange with a body.

The organ temperature can be estimated using temperature measurements on body parts of the patient. These body parts may include the skin, which is easily accessible, and body parts other than the skin. Because the skin is easily accessible, a number of temperature measurements may be performed on the skin, wherein the temperature can be measured at different locations on the skin of the body of the patient. The temperature of the skin may then be determined by taking the average of the measured skin temperatures.

In an embodiment of the method of the invention, the current organ temperature of the patient at a time t is estimated by measuring input parameters consisting of the skin temperature of the patient and the temperature of at least one body part of the patient other than the skin, and the power supplied to the heat exchanger prior to time t. Preferentially the at least one other body part comprises multiple organs, which form a basis of estimating the current brain temperature, wherein the other body part is represented by an organ temperature, and is used to form a basis to estimate a specific organ (e.g. brain) temperature.

Multiple input parameters increase the quality of measurement, since the measurement of the temperature of the skin can be compared to the temperature of other body parts. The at least one body part other than the skin preferably comprises the bladder, left tympanic, right tympanic, anus, pulmonary arteries, femoral veins, and/or oesophagus. These organs are available without extensive surgery. Also, having multiple input parameters creates redundancy. If one of the probes used to measure the temperature fails or provides non-reliable readings, a continuous accurate estimate of the organ temperature will be provided by using the other non-affected input parameters only. The treatments can continue while a technician corrects the problem. Therefore, in an embodiment, the input parameters comprise the temperature of at least five body parts of the patient other than the skin.

Each input parameter may comprise the temperature measured by a temperature sensor placed on a body part of the patient. Because the skin of a patient is easily accessible, a number of temperature sensors can, and preferably will, be placed on the skin. All other measurements can be measured relative to the skin, such that they provide, in combination with this skin measurement, input parameters for the parametric correlation.

In another embodiment of the present invention, the temperatures are measured simultaneously. The simultaneous measurement of the temperatures increases the accuracy of the estimation of the organ temperature and allows a real-time control.

In yet another embodiment, the input parameters comprise the body mass of the patient. In this embodiment, the mass of a patient is taken into account in estimating the organ temperature which allows a more accurate prediction of the organ temperature. Indeed, a heavier person will generally take more time to heat up or cool down, since the supplied heat or cold inside such a person can dissipate over a larger surface which results in a lower temperature change because a heavier patient has a higher heat capacity compared to a lighter patient. In the present embodiment, the body mass of the mammal on which the model was obtained is interchanged with the body mass of the patient.

In still another embodiment of the present invention the power supply to the heat exchanger is discontinued at a time t and the organ temperature after time t is estimated from the power supplied to the heat exchanger prior to time t. The power supply to the heat exchanger may for instance be discontinued when the controller suspects the future organ temperature to exceed or get close to a set threshold value, based on the calculated organ temperature estimate. The method in accordance with the present embodiment allows for estimating the future organ temperature on the basis of the power supplied to the heat exchanger before turning the heat exchanger off.

In another embodiment of the present invention the organ temperature at a time t is estimated by deriving an organ temperature at time t for each measured input parameter at time t, and taking the arithmetic mean of the derived organ temperatures for all measured input parameters to obtain the estimated organ temperature. This procedure yields an improved accuracy. For example, at a given time, the organ temperature is estimated using the measured temperature at the bladder, the right tympanic and the left tympanic. An accurate estimate of the organ temperature can then, in the present preferred embodiment, be obtained by taking the arithmetic mean of the three organ temperature estimates, each of which is based on the measured temperature in one of the named organs.

In another improved embodiment, the arithmetic mean does not include the highest and the lowest value of the organ temperature estimates for each temperature sensor. The accuracy of the estimation of the organ temperature can further be improved by eliminating the extreme measurements of the input parameters, since the extremes are more likely to contain faulty measurements. The present embodiment introduces redundancy and takes into account faulty measurements by eliminating extremes.

Another aspect of the invention provides a method for obtaining a model for estimating the temperature of an organ of a patient at a time t wherein the model comprises a parametric correlation function of the organ temperature and a number of input parameters. The method comprises creating a fluid circuit that comprises a mammal other than a patient, preferably an animal, and a heat exchanger, the power supply thereto being controlled by a controller; controlling the heat exchanger to a set temperature profile; subjecting at least a portion of the fluid in said circuit to the heat exchanger; directing the subjected fluid to and into the mammal to change the temperature of the mammal; measuring corresponding input parameters comprising the skin temperature of the mammal at a time t, the temperature of at least one body part of the mammal other than the skin temperature, and the power supplied to the heat exchanger prior to time t; measuring the organ temperature of the mammal at the time t; establishing a parametric correlation function between an estimated organ temperature of the mammal and the input parameters measured on the mammal, and determining the parameters of the parametric correlation function such that the difference between the estimated organ temperature calculated with the correlation function and the measured organ temperature is minimized. The method performed on the mammal, and preferably on an animal, serves to calibrate the parameters of the correlation function. In comparison with other animals the pig is a preferred animal on testing certain correlation functions also applicable in humans as a result of similarity of the circulation and weight; therefore giving an estimate of the accurate organ temperature in a human patient can well be based on measurements of relevant input parameters in pigs. In an embodiment, the weight of the mammal, preferably animal, is also measured and compared, and/or adjusted, to the weight of the patient, in order to achieve a better correlation.

A parametric correlation function to estimate organ temperature based on temperature measurements on other parts of the body can be made using a mammal other than a patient, preferably an animal. A similar fluid circuit can be made comprising the mammal and a heat exchanger, wherein the power supply to the heat exchanger is again controlled by a controller. The difference between the method as described earlier is that the organ temperature of the mammal is measured directly by a temperature sensor in the organ of the mammal. With the actual organ temperature and temperatures measured on other parts of the mammal, a correlation function can be derived. In order to increase the accuracy of this function, measurements are preferably performed on a mammal with similar physiological properties as a human, such as a pig. Other factors that may influence the estimated organ temperature, such as pump rate, flowing rates, environmental temperature and power of the heat exchanger for instance, could be considered in the parametric correlation function. In a preferred apparatus and method performed on a patient, the set values of these factors are chosen equal to, or about equal to the values that were used in performing the calibration method on a mammal.

In an embodiment of the present invention the parametric correlation function for one temperature sensor "i" is given by:

$$T_{organ}(t) = C_i + f_{skin} * T_{skin} + f_i * T^i_{sensor} + 1/M \Sigma f_{ij} * P(\Delta t_j)$$

wherein:
$T_{organ}(t)$=organ temperature at time t;
$C_i$=a parameter constant for sensor "i" (° C.);
$f_{skin}$=a parameter constant (–);
$T_{skin}$=the measured skin temperature (° C.);
$f_i$=a parameter constant (–) for the $i_{th}$ temperature sensor;
$T^i_{sensor}$=the measured temperature of the $i_{th}$ temperature sensor (° C.);
M=body mass of the patient (kg); and
$\Sigma f_{ij} * P(\Delta t_j)$=a weighted sum of the added/extracted energy in time intervals $\Delta t_j = t_j - t_{j-1}$ prior to time t with $f_{ij}$=parameter constant for each $j_{th}$ time interval.

In this function the estimated organ temperature at time t depends on a constant, the temperature of the skin, the measured temperature of another body part and a weighted sum of the power supplied by the heat exchanger prior to time t, wherein the time lag between supplying power to the heat exchanger and increase of the organ temperature is weighted with the body mass of the patient. The weighing factors in the sum are obtained by calibration on a mammal or animal. The input parameters (such as the measured temperatures) are preferably measured at the same or at least similar body parts of the patient as on the mammal or animal used to calibrate the model.

The estimation of the organ temperature can be repeated regularly, for instance every couple of seconds. Doing so provides a moving estimate of the actual and future organ temperatures. Based on these temperatures it can be determined whether the organ temperatures could exceed a critical threshold value. If that appears to be so, the power supply to the heat exchanger may be decreased, while measurements and organ temperature estimations continue. If the estimated organ temperature remains below the critical threshold value for a predetermined period of time, the power supply to the heat exchanger may be increased.

The organ temperature at a time t can be estimated by deriving a organ temperature at time t for one temperature sensor "i" with the parametric correlation function and taking the arithmetic mean of the derived organ temperatures for all input parameters to obtain the estimated organ temperature, for instance taking the arithmetic mean of the derived organ temperature based on the temperature of the bladder, the derived organ temperature based on the temperature of the oesophagus and the derived organ temperature based on the temperature of the right ear.

In an embodiment of the present invention the constants C, $f_{skin}$, $f_i$ and $f_j$ of the parametric function are obtained by a method using a mammal. The obtained parameter values are then used in estimating an organ's temperature in a patient. The parameter values are organ specific. For instance, the values may be different when estimating brain temperature as compared to estimating kidney temperature or any other organ temperature. According to the invention, the organ of which the temperature is estimated, as well as the input parameters and model parameter constants are preferably the same between a calibration mammal and a patient.

A further improved embodiment of the method for obtaining the predictive model comprises a parametric correlation function for one temperature sensor "i" given by:

$$T_{organ}(t) = C_i + f_i \cdot T^i_{sensor} + 1/M \int f_j \cdot Q(t) \cdot (T_{fin} - T_{fout}) dt$$

wherein
- $T_{organ}(t)$ = organ temperature at time t;
- $C_i$ = a parameter constant for sensor "i" (° C.);
- $f_i$ = a parameter constant (–) for the $i_{th}$ temperature sensor;
- $T^i_{sensor}$ = the measured temperature of the $i_{th}$ temperature sensor (° C.);
- M = body mass of the mammal (kg);
- $\int f_j \cdot Q(t) \cdot (T_{fin} - T_{fout}) dt$ = the integral from $t_j$ to $t_{j-1}$ of the product of the fluid flow Q (in m³/sec) and the temperature difference between the measured temperature $T_{fin}$ of the fluid (° C.) when entering the body and the measured temperature $T_{fout}$ of the fluid (° C.) when exiting the body in time intervals $\Delta t_j = t_j - t_{j-1}$ prior to time t with $f_j$ = parameter constant for each $j_{th}$ time interval.

Yet another embodiment of the method for obtaining the predictive model comprises a parametric correlation function for one temperature sensor "i" given by:

$$T_{organ}(t) = C_i + T_{estimate}(0) + f_i \cdot (T^i_{sensor} - T^{i0}_{sensor}) + 1/M \Sigma f_j \cdot P(\Delta t_j)$$

wherein
- $T_{organ}(t)$ = organ temperature at time t;
- $C_i$ = a parameter constant for sensor "i" (° C.);
- $T_{estimate}(0)$ = the estimated organ temperature at time 0;
- $f_i$ = a parameter constant (–) for the $i_{th}$ temperature sensor;
- $T^i_{sensor}$ = the measured temperature of the $i_{th}$ temperature sensor (° C.);
- $T^{i0}_{sensor}$ = the measured temperature of the $i_{th}$ temperature sensor (° C.) at time 0;
- M = body mass of the mammal (kg);
- $\Sigma f_j \cdot P(\Delta t_j)$ = a weighted sum of the heat outputs of the heat exchanger in time intervals $\Delta t_j = t_j - t_{j-1}$ prior to time t with $f_j$ = parameter constant for each $j_{th}$ time interval.

The invention also relates to an apparatus suited to carry out any method according to the present invention. According to the invention, an apparatus for controlling the inner temperature of a patient is provided, the apparatus comprising at least one catheter for creating a fluid circuit external to the patient; a pump in association with said catheter, for pumping a fluid through said fluid circuit and the patient; a heat exchanger through which said fluid circuit flows for influencing the temperature of said fluid; a controller arranged to estimate an organ temperature of said patient and control the power supplied to the heat exchanger based on the estimated organ temperature, wherein the organ temperature is estimated by a model that has been obtained on a mammal other than the patient.

In another embodiment of the present invention the apparatus is usable when patients are subjected to whole body hyperthermia. The invention therefore also relates to an apparatus for controlling the inner temperature of a patient when subject to whole body hyperthermia, comprising a device to subject the patient to whole body hyperthermia, comprising: at least one catheter for creating a fluid circuit external to the patient; a pump in association with said catheter, for pumping the fluid; a heat exchanger through which said fluid circuit flows; and a controller, arranged to estimate organ temperature and control the power supply to the heat exchanger wherein the controller controls the power supplied to the heat exchanger based on the estimated organ temperature.

The apparatus may also comprise at least two temperature sensors, for measuring the temperature of a patient on multiple locations on the body of the patient and estimate the organ temperature based on measurements from the temperature sensors The pump is used to pump fluid in the patient at a rate for instance slightly less than the pump rate of the heart of the patient, for instance around 1.5 litres of fluid per minute for a 75 kg patient. The heat exchanger used in such an apparatus is typically used as a heater, but could also be used to cool down the fluid (typically blood) running through the fluid circuit.

Multiple temperature sensors allow for reliable temperature measurements, since faulty sensors can be recognized because their predicted values will deviate strongly from the proper sensors, and the value from properly functioning sensors can be averaged. Multiple sensors also allow accurate temperature measurements, since it allows for temperature averaging. The temperature sensors may be arranged to be placed on the body parts according to the present invention, for instance the bladder, the skin, left tympanic, right tympanic, anus, pulmonary arteries, femoral veins, and/or oesophagus.

In an embodiment of the apparatus the controller is arranged to estimate the organ temperature of the patient based on signals from the multiple temperature sensors and controlling the power supply to the heat exchanger such that the estimated organ temperature remains below a threshold brain temperature.

According to another embodiment of the invention, an apparatus is provided wherein the model comprises a parametric correlation function of the temperature of the organ and a number of input parameters.

Another embodiment of the apparatus according to the invention comprises at least two temperature sensors for measuring the temperature of multiple body parts of the patient, wherein the controller is arranged to estimate the organ temperature by measuring input parameters comprising the temperature of the at least two temperature sensors, and the power supplied to the heat exchanger prior to time t.

Yet another embodiment of the apparatus according to the invention comprises at least two temperature sensors for measuring the temperature of the patient on multiple locations on the body of the patient, means for measuring the flow rate of the fluid, as well as means for measuring the temperature of the fluid when entering and exiting the patient, wherein the controller is arranged to estimate the organ temperature by measuring input parameters comprising the temperature of the at least two temperature sensors, the fluid flow rate into the patient and the fluid temperatures entering and exiting the patient.

Another useful embodiment of the apparatus according to the invention comprises at least two temperature sensors for measuring the temperature of the patient on multiple locations on the body of the patient, wherein the controller is arranged to estimate the organ temperature by measuring input parameters comprising the temperature of the at least two temperature sensors at time 0, and the estimated organ temperature at time 0.

The apparatus according to another embodiment of the invention y comprises a heat exchanger in the form of a heater and/or a cooler.

In a further embodiment of the apparatus according to the invention the at least two temperature sensors are arranged to be placed at one of the following locations: the bladder, the skin, left tympanic, right tympanic, anus, pulmonary arteries, femoral veins, and/or oesophagus.

Yet another embodiment of the apparatus according to the invention is characterized in that the controller is arranged to estimate the organ temperature of the patient based on signals from the temperature sensors and controlling the power supply to the heat exchanger such that the estimated organ temperature remains below an upper threshold organ temperature and/or above a lower threshold organ temperature. Preferably, the controller is arranged to measure the temperatures simultaneously.

Accurate results are obtained in an embodiment of the apparatus according to the invention wherein the input parameters comprise the body mass of the patient.

Another embodiment of the invention provides an apparatus wherein the controller is arranged to discontinue the power supply to the heat exchanger at a time t and to estimate the future organ temperature after time t from the power supplied to the heat exchanger prior to time t.

Yet another embodiment of the invention provides an apparatus wherein the controller is arranged to estimate the organ temperature at a time t by deriving the organ temperature at time t for each input parameter, and taking the arithmetic mean of the derived organ temperatures for all input parameters to obtain the estimated organ temperature.

The arithmetic mean may be unweighted, but preferably is a weighted arithmetic mean, for instance weighted with the reciprocal of the variance. Another preferred embodiment relates to an apparatus wherein the arithmetic mean does not include the highest and the lowest value of the derived organ temperatures for each temperature measured.

A useful embodiment of the invention provides an apparatus wherein the parametric correlation function for one temperature sensor "i" is given by:

$$T_{organ}(t) = C_i + f_{skin} \cdot T_{skin} + f_i \cdot T^i_{sensor} + 1/M \Sigma f_j \cdot P(\Delta t_j)$$

wherein
$T_{organ}(t)$=organ temperature at time t;
$C_i$=a parameter constant for sensor "i" (° C.);
$f_{skin}$=a parameter constant (–);
$T_{skin}$=the measured skin temperature (° C.);
$f_i$=a parameter constant (–) for the $i_{th}$ temperature sensor;
$T^i_{sensor}$=the measured temperature of the $i_{th}$ temperature sensor (° C.);
M=body mass of the patient (kg);
$\Sigma f_j \cdot P(\Delta t_j)$=a weighted sum of the heat outputs of the heat exchanger in time intervals $\Delta t_j = t_j - t_{j-1}$ prior to time t with $f_j$=parameter constant for each $j_{th}$ time interval.

The correlation function of choice corresponds with the correlation function obtained on a mammal, but the body mass of the mammal is interchanged with the body mass of the patient.

Another useful embodiment relates to an apparatus wherein the parametric correlation function for one temperature sensor "i" is given by:

$$T_{organ}(t) = C_i + f_i \cdot T^i_{sensor} + 1/M \int f_j \cdot Q(t) \cdot (T_{fin} - T_{fout}) dt$$

wherein
$T_{organ}(t)$=organ temperature at time t;
$C_i$=a parameter constant for sensor "i" (° C.);
$f_i$=a parameter constant (–) for the $i_{th}$ temperature sensor;

$T^i_{sensor}$=the measured temperature of the $i_{th}$ temperature sensor (° C.);
M=body mass of the patient (kg);
$\int f_j \cdot Q(t) \cdot (T_{fin} - T_{fout}) dt$=the integral from $t_j$ to $t_{j-1}$ of the product of the fluid flow Q (in m³/sec) and the temperature difference between the measured temperature $T_{fin}$ of the fluid (° C.) when entering the body and the measured temperature $T_{fout}$ of the fluid (° C.) when exiting the body in time intervals $\Delta t_j = t_j - t_{j-1}$ prior to time t with $f_j$=parameter constant for each $j_{th}$ time interval.

This embodiment takes account of any additional heat input from other parts of the apparatus than the heat exchanger. The heat input is indirectly measured by measuring the fluid flow rate through the fluid circuit and by measuring the fluid temperature entering and exiting the body of the patient. In the calibration method carried out on mammals, the patient is interchanged with the mammal.

In yet another embodiment of the invention, an apparatus is provided wherein the parametric correlation function for one temperature sensor "i" is given by:

$$T_{organ}(t) = C_i + T_{estimate}(0) + f_i \cdot (T^i_{sensor} - T^{i0}_{sensor}) + 1/M \Sigma f_j \cdot P(\Delta t_j)$$

wherein
$T_{organ}(t)$=organ temperature at time t;
$C_i$=a parameter constant for sensor "i" (° C.);
$T_{estimate}(0)$=the estimated organ temperature at time 0;
$f_i$=a parameter constant (–) for the $i_{th}$ temperature sensor;
$T^i_{sensor}$=the measured temperature of the $i_{th}$ temperature sensor (° C.);
$T^{i0}_{sensor}$=the measured temperature of the $i_{th}$ temperature sensor (° C.) at time 0;
M=body mass of the patient (kg);
$\Sigma f_j \cdot P(\Delta t_j)$=a weighted sum of the heat outputs of the heat exchanger in time intervals $\Delta t_j = t_j - t_{j-1}$ prior to time t with $f_j$=parameter constant for each $j_{th}$ time interval.

This embodiment measures temperatures at time 0, i.e. at a time before actually starting the treatment and directing heated fluid to and into a patient. In this way, due account is taken of the fact that the core body temperature of an animal at rest, in particular a pig, may vary considerably between animals. Core body temperatures between humans are generally considered to differ less or even to be negligible.

Although a fluid such as saline may be used in the apparatus and method according to the invention, blood is the preferred fluid.

The present invention is further elucidated on the basis of the non-limitative exemplary embodiment shown in the following figures. Herein shows:

FIG. 1 a schematic representation of an apparatus in accordance with the present invention FIG. 1 shows an apparatus (1) for controlling the temperature in a patient (2), comprising two catheters (3,4), one (3) for blood exiting the patient, and one (4) for returning the blood to the patient, for creating a fluid circuit (5) external to the patient; a pump (6) in association with said catheters, for pumping the fluid; a heat exchanger (7) through which said fluid circuit flows; and a controller (8), arranged to control the heater exchanger. In accordance with the invention, the controller controls the heat exchanger based on an estimated brain (9) temperature.

The temperature of the brain is estimated based on temperature measurements on multiple locations on the patient, comprising, in this example, four temperature sensors (10, 11, 12, 13) located at the left tympanic (10), right tympanic (11), the bladder (12) and the skin (13). The temperature sensors can feed the measured temperatures to the controller to obtain the estimated brain temperature.

Calibration Method

The following method according to the invention was performed wherein the heat exchanger was a heater, and the organ was the brain. A pig was subjected to a method in which a fluid circuit was created comprising the pig and a heater, the power supply thereto being controlled by a controller, by using the apparatus of FIG. 1. The heater was controlled to a set temperature profile, and the fluid in the circuit heated by the heater. The heated fluid was then directed to and into the pig to change the temperature of the pig. Input parameters comprising the skin temperature of the pig at a time t, the temperature of selected body parts of the pig other than the skin temperature, and the power supplied to the heater prior to time t were measured at discrete intervals. A temperature sensor was applied to the pig's brain to measure the brain temperature continuously at different times t.

The following parametric correlation function between an estimated brain temperature of the animal and the input parameters measured on the animal was established:

$$T_{brain}(t)=C_i+f_{skin}*T_{skin}+f_i*T^i_{sensor}+1/M\Sigma f_j*P(\Delta t_j)$$

The parameters of the parametric correlation function were calculated such that the difference between the estimated brain temperature calculated with the correlation function and the measured brain temperature is minimized.

The following parameter values were obtained:
$C_i$=9.6362 (° C.);
$f_{skin}$=0.03 (−);
$f_i$=0.7296 (° C.);

EXAMPLE 1

The obtained parameters were used in the above mentioned function and applied to a situation wherein a patient was subjected to the same method as the pig, except for the placement of the sensor inside the brain. The temperature of the patient was measured on the skin and one other location.

The following values are measured by sensors during whole body hyperthermia of the patient:
$T_{skin}$=40.2305 (° C.);
$T^i_{sensor}$=42.9612 (° C.);
The mass of the patient was 65.0 kg.

4 prior heat outputs were considered in the weighted sum of the parametric function, wherein the time intervals of 60 seconds were used:
$f_1$=0.0192 with a P(0-60) of 3.2756 kJ
$f_2$=0.0072 with a P(60-120) of 1.133 kJ
$f_3$=0.0111 with a P(120-180) of 94.400 kJ
$f_4$=0.0240 with a P(180-240) of 157.1333 kJ When all these values are entered in the function, the estimated brain temperature based on one sensor besides the skin temperature sensor is 42.26° C. The controller may, based on this value and given that this value is below the threshold value of 43° C., determine if more power should be supplied to the heater to increase the body temperature of the patient.

EXAMPLE 2

In this example the organ was again the brain, and the heat exchanger was set up to be a heater. An estimation of the future brain temperature will be described. The future brain temperature can be a measure to estimate if threshold values are exceeded if power supply to the heater is discontinued for a certain amount of time. Because it takes a certain amount of time before the heat supplied by the heater affects the brain temperature, the expected future brain temperature depends on the added heat before that time.

If from time t no more heat is supplied to the heater, the same function as derived in the calibration method can be used to determine the expected brain temperature in the future, with a small alteration in the weighted sum of heat outputs $(1/M\Sigma f_j*P(\Delta t_j))$.

The 4 prior heat outputs of Example 1 will shift one position, since the future brain temperature is estimated.

In the weighted sum the time intervals then become the following:
$f_1$=0.000 with a P(0-60) of 0 (heater was switched off, weighing factor is irrelevant now, anything multiplied with zero becomes zero)
$f_2$=0.0072 with a P(0-60) of 3.2756 kJ ($f_1$ of example 1)
$f_3$=0.0111 with a P(60-120) of 1.133 kJ ($f_2$ of example 1)
$f_4$=0.0240 with a P(120-180) of 94.400 kJ ($f_3$ of example 1)

The other values remain the same, yielding an estimated future brain temperature of 42.22° C., based on previous added heat and when heating is switched off for one period of time.

The invention claimed is:

1. An apparatus for controlling an inner temperature of a human patient that is subjected to whole body hyperthermia, the apparatus comprising:
   two catheters for creating a fluid circuit external to the human patient, wherein one catheter is for exiting a fluid from the human patient and the other catheter is for returning said fluid to the human patient, wherein said fluid is blood;
   at least two temperature sensors for measuring a temperature of said human patient on multiple locations on the body of the human patient, wherein the temperature sensors are not located in the brain;
   a pump in association with said catheters, for pumping said fluid through said fluid circuit and the human patient;
   a heat exchanger through which said fluid circuit flows for influencing the temperature of said fluid;
   a controller arranged to estimate an organ temperature of the human patient, wherein the organ is the brain, and control the power supplied to the heat exchanger based on the estimated organ temperature of the human patient such that the estimated organ temperature of the human patient remains below an upper threshold organ temperature of the human patient, wherein the organ temperature of the human patient is estimated by a model comprising a parametric correlation function of the temperature of the organ and a number of input parameters, said input parameters including the body mass of the human patient and temperature measurements on multiple locations on the body based on signals from said two temperature sensors, wherein the parametric correlation function, including the calibration of the parameters of the correction function, has been obtained on an animal other than the human patient, by:
   creating a fluid circuit that comprises the animal and a heat exchanger, the power supply thereto being controlled by a controller;
   controlling the heat exchanger to set a temperature profile;

subjecting at least a portion of the fluid in said fluid circuit to the heat exchanger;
directing the subjected fluid to and into the animal to change the temperature of the animal;
measuring corresponding input parameters comprising the temperature of at least one body part of the animal at a time t, and the power supplied to the heat exchanger prior to time t;
measuring the organ temperature of the animal at the time t, wherein the organ is the brain;
establishing a parametric correlation function between an estimated organ temperature of the animal and the input parameters measured on the animal, wherein the estimated organ temperature of the animal is an estimated brain temperature of the animal, and
determining the model parameters of the parametric correlation function such that the difference between the estimated organ temperature of the animal calculated with the correction function and the measured organ temperature of the animal is minimized.

2. The apparatus according to claim 1, wherein the controller is arranged to estimate the organ temperature of the human patient by measuring input parameters comprising the temperature of the at least two temperature sensors, and the power supplied to the heat exchanger prior to time t.

3. The apparatus according to claim 1, comprising means for measuring the flow rate of the fluid, as well as means for measuring the temperature of the fluid when entering and exiting the patient, wherein the controller is arranged to estimate the organ temperature by measuring input parameters comprising the temperature of the at least two temperature sensors, the fluid flow rate into the human patient and the fluid temperatures entering and exiting the human patient.

4. The apparatus according to claim 1, wherein the controller is arranged to estimate the organ temperature of the human patient by measuring input parameters comprising the temperature of the at least two temperature sensors at time 0, and the estimated organ temperature of the human patient at time 0.

5. The apparatus according to claim 1, wherein the heat exchanger is a heater and/or a cooler.

6. The apparatus according to claim 1, wherein the at least two temperature sensors are arranged to be placed at one of the following locations: the bladder, the skin, left tympanic, right tympanic, anus, pulmonary arteries, femoral veins, and/or esophagus.

7. The apparatus according to claim 1, wherein the controller is arranged to estimate the organ temperature of the human patient based on signals from the temperature sensors and controlling the power supply to the heat exchanger such that the estimated organ temperature remains below an upper threshold organ temperature of the human patient and/or above a lower threshold organ temperature of the human patient.

8. The apparatus according to claim 1, wherein the controller is arranged to measure the temperatures on the multiple locations on the body simultaneously with the at least two temperature sensors.

9. The apparatus according to claim 1, wherein the controller is arranged to discontinue the power supply to the heat exchanger at a time t and to estimate a future organ temperature of the human patient after time t from the power supplied to the heat exchanger prior to time t.

10. The apparatus according to claim 1, wherein the controller is arranged to estimate the organ temperature of the human patient at a time t by deriving the organ temperature of the human patient at time t for each input parameter, and taking the arithmetic mean of the derived organ temperatures for all input parameters to obtain the estimated organ temperature of the human patient.

11. The apparatus according to claim 10, wherein the arithmetic mean does not include the highest and the lowest value of the derived organ temperatures of the human patient for each temperature measured.

12. The apparatus according to claim 1, wherein the parametric correlation function for each temperature sensor "i" of the at least two temperature sensors is given by:

$$T^i_{organ}(t) = C_i + f_{skin} \cdot T_{skin} + f_i \cdot T^i_{sensor} + 1/M \Sigma f_j \cdot P(\Delta t_j)$$

wherein
$T^i_{organ}(t)$=estimated organ temperature of the human patient at time t;
$C_i$=a parameter constant for sensor "i" (° C.);
$f_{skin}$=a parameter constant (–);
$T_{skin}$=the measured skin temperature of the human patient;
$f_i$=a parameter constant (–) for the $i_{th}$ temperature sensor (C);
$T^i_{sensor}$=the measured temperature of the $i_{th}$ temperature sensor (C;
M=body mass of the human patient (kg);
$\Sigma f_j \cdot P(\Delta t_j)$=a weighted sum of the heat outputs of the heat exchanger in time intervals $\Delta t_j = t_j - t_{j-1}$ prior to time t with $f_j$=parameter constant for each $j_{th}$ time interval, and wherein the estimated organ temperature $T_{organ}(t)$ of the human patient is the arithmetic mean of the estimates of the at least two temperature sensors.

13. The apparatus according to claim 1, wherein the parametric correlation function for each temperature sensor "i" of the at least two temperature sensors is given by:

$$T^i_{organ}(t) = C_i + f_{skin} * T^i_{sensor} + 1/M \int f_j \cdot Q(t) \cdot (T_{fin} - T_{fout}) dt$$

wherein
$T^i_{organ}(t)$=estimated organ temperature of the human patient at time t;
$C_i$=a parameter constant for sensor "i" (° C.);
$f_i$=a parameter constant (–) for the $i_{th}$ temperature sensor;
$T^i_{sensor}$=the measured temperature of the $i_{th}$ temperature sensor (° C.);
M=body mass of the human patient (kg);
$\int f_j \cdot Q(t) \cdot (T_{fin} - T_{fout}) dt$=the integral from $t_j$ to $t_{j-1}$ of the product of the fluid flow Q (in m$^3$/sec) and the temperature difference between the measured temperature $T_{fin}$ of the fluid (° C.) when entering the body and the measured temperature
a weighted sum of the heat outputs of the heat exchanger in time intervals $\Delta t_j = t_j - t_{j-1}$ prior to time t with $f_j$=parameter constant for each $j_{th}$ time interval, and wherein the estimated organ temperature $T_{organ}(t)$ of the human patient is the arithmetic mean of the estimates of the at least two temperature sensors.

14. The apparatus according to claim 1, wherein the parametric correlation function for each temperature sensor "i" of the at least two temperature sensors is given by:
$T^i_{organ}(t) = C_i + T_{estimate}(0) + f_i \cdot (T^i_{sensor} - T^{i0}_{sensor}) + 1/M \Sigma f_j \cdot P(\Delta t_j)$
wherein
$T^i_{organ}(t)$=estimated organ temperature of the human patient at time t;
$C_i$=a parameter constant for sensor "i" (° C.);
$T_{estimate}(0)$=the estimated organ temperature at time 0;

$f_i$=a parameter constant (−) for the $i_{th}$ temperature sensor (° C.);
$T^i_{sensor}$=the measured temperature of the $i_{th}$ temperature sensor (° C.);
$T^{i0}_{sensor}$=the measured temperature of the $i_{th}$ temperature sensor (° C.) at time 0;
M=body mass of the human patient (kg);
$\Sigma f_j \cdot P(\Delta t_j)$=a weighted sum of the heat outputs of the heat exchanger in time intervals $\Delta t_j = t_j - t_{j-1}$ prior to time t with $f_j$=parameter constant for each $j_{th}$ time interval,
and wherein the estimated organ temperature $T_{organ}(t)$ of the human patient is the arithmetic mean of the estimates of the at least two temperature sensors.

* * * * *